US007758547B2

(12) United States Patent
Tonelli et al.

(10) Patent No.: US 7,758,547 B2
(45) Date of Patent: Jul. 20, 2010

(54) PROCESS FOR CONTROLLING AN INFUSION DEVICE

(75) Inventors: Claudio Tonelli, Modena (IT); Andrea Ligabue, San Prospero (IT); Silvano Cestari, San Felice sul Panaro (IT)

(73) Assignee: Gambro Lundia AB, Lund (SE)

( * ) Notice: Subject to any disclaimer, the term of this patent is extended or adjusted under 35 U.S.C. 154(b) by 1346 days.

(21) Appl. No.: 11/104,446

(22) Filed: Apr. 13, 2005

(65) Prior Publication Data

US 2005/0234387 A1 Oct. 20, 2005

Related U.S. Application Data

(60) Provisional application No. 60/522,439, filed on Oct. 1, 2004.

(30) Foreign Application Priority Data

Apr. 20, 2004 (TW) ..................... MO2004A000086

(51) Int. Cl.
*A61M 37/00* (2006.01)
*A61N 1/30* (2006.01)
*A61M 31/00* (2006.01)
*F04B 49/00* (2006.01)
*B67D 1/00* (2006.01)
*B67D 7/14* (2006.01)

(52) U.S. Cl. ..................... 604/131; 604/4.01; 604/6.11; 604/6.16; 604/19; 604/48; 604/500; 604/65; 604/73; 604/93.01; 417/18; 417/25; 417/63; 222/55; 222/62; 222/63; 222/333

(58) Field of Classification Search ................... 604/19, 604/500, 514, 65, 67, 118, 121, 66; 128/DIG. 12, 128/DIG. 13; 417/18, 25, 63; 222/55, 61, 222/63, 333
See application file for complete search history.

(56) References Cited

U.S. PATENT DOCUMENTS

| | | | | |
|---|---|---|---|---|
| 4,137,913 A * | 2/1979 | Georgi | ......................... | 604/67 |
| 4,444,546 A | 4/1984 | Pazemenas | | |
| 5,106,375 A * | 4/1992 | Conero | ....................... | 604/155 |
| 5,176,502 A * | 1/1993 | Sanderson et al. | ............ | 417/18 |
| 5,599,301 A * | 2/1997 | Jacobs et al. | ................... | 604/65 |
| 5,814,015 A * | 9/1998 | Gargano et al. | ............... | 604/67 |
| 6,200,289 B1 * | 3/2001 | Hochman et al. | ............. | 604/67 |
| 6,221,045 B1 * | 4/2001 | Duchon et al. | .............. | 604/151 |
| 6,423,035 B1 * | 7/2002 | Das et al. | ..................... | 604/155 |
| 2002/0009385 A1 * | 1/2002 | Krivitski et al. | ............... | 422/44 |

(Continued)

*Primary Examiner*—Leslie R. Deak
*Assistant Examiner*—Adam Marcetich
(74) *Attorney, Agent, or Firm*—Rissman Hendricks & Oliverio, LLP (57) ABSTRACT

A process comprises the phases of: activating a pusher, which exerts a push force on a plunger of a syringe containing the infusion liquid; measuring the push force by means of a load cell; comparing the push force with a maximum threshold; halting the pusher when the maximum threshold is exceeded; after a predetermined pause, restarting the pusher and emitting a consent signal indicating correct loading of the syringe if, within a certain time from the restart, the push force again exceeds the maximum threshold. The infusion device serves to inject an anticoagulant into an extracorporeal blood circuit. The control process guarantees against loss of infusion due to an incorrect initial loading of the syringe.

30 Claims, 4 Drawing Sheets

U.S. PATENT DOCUMENTS

2002/0052574 A1* 5/2002 Hochman et al. ............. 604/31
2002/0128594 A1* 9/2002 Das et al. ..................... 604/67
2003/0171712 A1 9/2003 Critchlow et al.
2003/0225371 A1* 12/2003 Hadzic et al. ............... 604/118

* cited by examiner

PROCESS FOR CONTROLLING AN INFUSION DEVICE

CROSS-REFERENCE TO RELATED APPLICATIONS

This application claims the benefit of priority of U.S. provisional application No. 60/522,439, filed Oct. 1, 2004, and Italian patent application no. MO2004A000086, filed Apr. 20, 2004, both of which are incorporated herein by reference in their entirety.

BACKGROUND OF THE INVENTION

The invention relates to a process for controlling an infusion device, in particular for controlling an infusion device of a type comprising a syringe for medical fluids.

Specifically, though not exclusively, the invention can be usefully applied for controlling a correct positioning, on a machine for extracorporeal blood treatment, of a variable-volume container containing the infusion liquid. In a specific use, the infusion device is for injecting an anti-coagulant into an extracorporeal blood circuit at very low-flow delivery rates.

Extracorporeal treatments usually include removal of blood from a patient, treatment of the blood externally of the human body and reintroduction of the blood into circulation.

Extracorporeal blood is made to circulate through a circuit comprising, in general, an arterial line, or blood removal line, which takes the blood from the patient to a blood treatment device (for example a dialyzer filter) and a venous line, or blood return line, which returns the treated blood to the patient.

To reduce the risk of coagulation of the extracorporeal blood, a known method includes infusion of an anticoagulant (for example heparin) into the extracorporeal circuit, generally into the arterial line, through an infusion line, with relatively low infusion flow rates.

An infusion device which is typically used in this method is a syringe pump, wherein a pushing element, on command of a linear actuator, pushes the plunger of a syringe containing the anticoagulant at an advancement rate which is predetermined and relatively slow. For example, in a dialysis treatment, usually the syringe contains the quantity of anticoagulant necessary for several hours of treatment. The pushing element and the actuator are part of the extracorporeal treatment machine (for example the dialysis machine), while the syringe is generally of the single-use type, or in any case is of the disposable type.

One of the problems of infusion devices having variable-volume containers, such as for example pumps or syringes used for administering an anticoagulant into an extracorporeal blood circuit, concerns the correct positioning of the variable-volume container (syringe) containing the anticoagulant liquid.

An incorrect positioning can be due to various causes, such as, for example:

absence of the syringe;

absence of contact between the syringe plunger and the pushing element, where the pushing element is a part of the infusion device predisposed for exerting a push on a mobile part (plunger) of the syringe to cause the infusion of the liquid contained in the syringe cylinder, in contrast with the action of the extracorporeal circuit pressure;

absence of a connection, or a poor and wrong connection of the syringe cylinder to the cylinder support.

In relation especially to the second above-cited cause, it is important that the pushing element, immediately after having received the command to start infusion of the anticoagulant liquid, is in stable contact with the mobile part (plunger), and so is able to perform the infusion force.

A failure in infusion, caused by absence of the above-described contact, might be prolonged, even if the positioning is only slightly wrong, given the low infusion flow rate and thus the extreme slowness of the pusher advancement. In a situation such as this, for example, a distance of one millimeter between the pusher and the plunger might cause a delay of several hours in the start of the infusion, with a consequent considerable risk of the formation of large clots in the extracorporeal blood.

Control of the correct positioning of the variable-volume container is at present performed by means of a visual inspection on the part of the operator, who checks if the pusher of the infusion device is in contact with the syringe plunger before initiating the administration of anticoagulant.

To do this, the operator positions the syringe in the appropriate seating predisposed on the machine, then advances the pusher gradually (for example by manually activating a command advance button on the front of the machine), up until he or she can see that contact between the pusher and the syringe has been achieved. At this point the infusion device is considered to be ready for dispensing the anticoagulant liquid.

This solution, however, exhibits various limitations and drawbacks, among which the risk of error on the part of the operator and the fact of complicating the stages necessary for readying an extracorporeal circuit.

SUMMARY OF THE INVENTION

An aim of the present invention is to provide a simple and reliable process for controlling correct operation of an infusion device.

A further aim of the invention is to realise a device which is simple, economical and able to actuate the process.

A further aim is to make available a machine for extracorporeal blood treatment which is provided with a safe and reliable infusion device for an anticoagulant.

An advantage of the invention is that it guarantees correct readying of the infusion device.

A further advantage of the invention is that it guarantees against loss of infusion, in particular during the initial stage of administration of the infusion liquid.

A further advantage is that it simplifies the readying operations for the infusion device.

A further advantage is that it automatically controls the correct readying of the infusion device, and thus prevents the risk of a wrong signal of correct readying in cases of, for example, accidental impacts on the device, incorrect and unforeseen manoeuvres thereof, disturbances in the electrical signal monitoring the operativity of the pusher.

These aims and advantages and more besides are all attained by the invention, as it is characterised in one or more of the appended claims.

In a specific embodiment, correct readying of the infusion device is recognised if, after an infusion force has satisfied a prefixed relation a first time, and after having ordered an interruption in operation of the infusion actuator, the infusion force satisfies a prefixed relation a second time.

In a specific embodiment of the invention, the correct reciprocal positioning between the container of the infusion liquid and the actuator which exerts the force able to cause the infusion is controlled by means of a procedure which comprises the stages of: monitoring the infusion force (or a parameter which is indicative of the force), providing the actuator with a first command signal when the infusion force satisfies a prefixed relation with a reference value; after a predefined time providing the actuator with a second command signal, different from the first, and then emitting a consent signal only if, after emission of the second command signal, the infusion force satisfies a prefixed relation with a reference value.

In a specific embodiment of the invention, the first command signal is a block or slowdown signal to the actuator, while the second command signal is a re-start or accelerate signal to the actuator.

In an embodiment of the invention, the first command signal is sent if the infusion force exceeds a predefined threshold.

In an embodiment of the invention, an alarm signal is emitted if, after a predetermined time, the prefixed relation is not satisfied.

In a specific embodiment, the two above-described prefixed relations, one conditioning the first control signal and the other conditioning the consent signal, are the same as each other.

In a specific embodiment, the control procedure is commanded automatically by a programmed controller.

In a specific embodiment, initially the actuator of the infusion device is manually commanded by an operator, in order to perform a gradual advancement of a pusher provided for exerting the infusion force.

In a specific embodiment, the infusion device is operatively associated to an extracorporeal blood circuit.

In a specific embodiment, the infusion device is a syringe pump, used in particular for infusing an anticoagulant into the blood at slow rates.

In an embodiment of the invention, the infusion device comprises a pusher which presses on a mobile part of a variable-volume container containing the infusion liquid.

Further characteristics and advantages of the present invention will better emerge from the detailed description that follows, of at least one preferred embodiment of the invention, illustrated by way of non-limiting example in the accompanying figures of the drawings.

BRIEF DESCRIPTION OF THE DRAWINGS

The description will be made herein below with reference to the figures of the drawings, which are intended as non-limiting examples of the invention, and in which.

DETAILED DESCRIPTION

Figure 1:
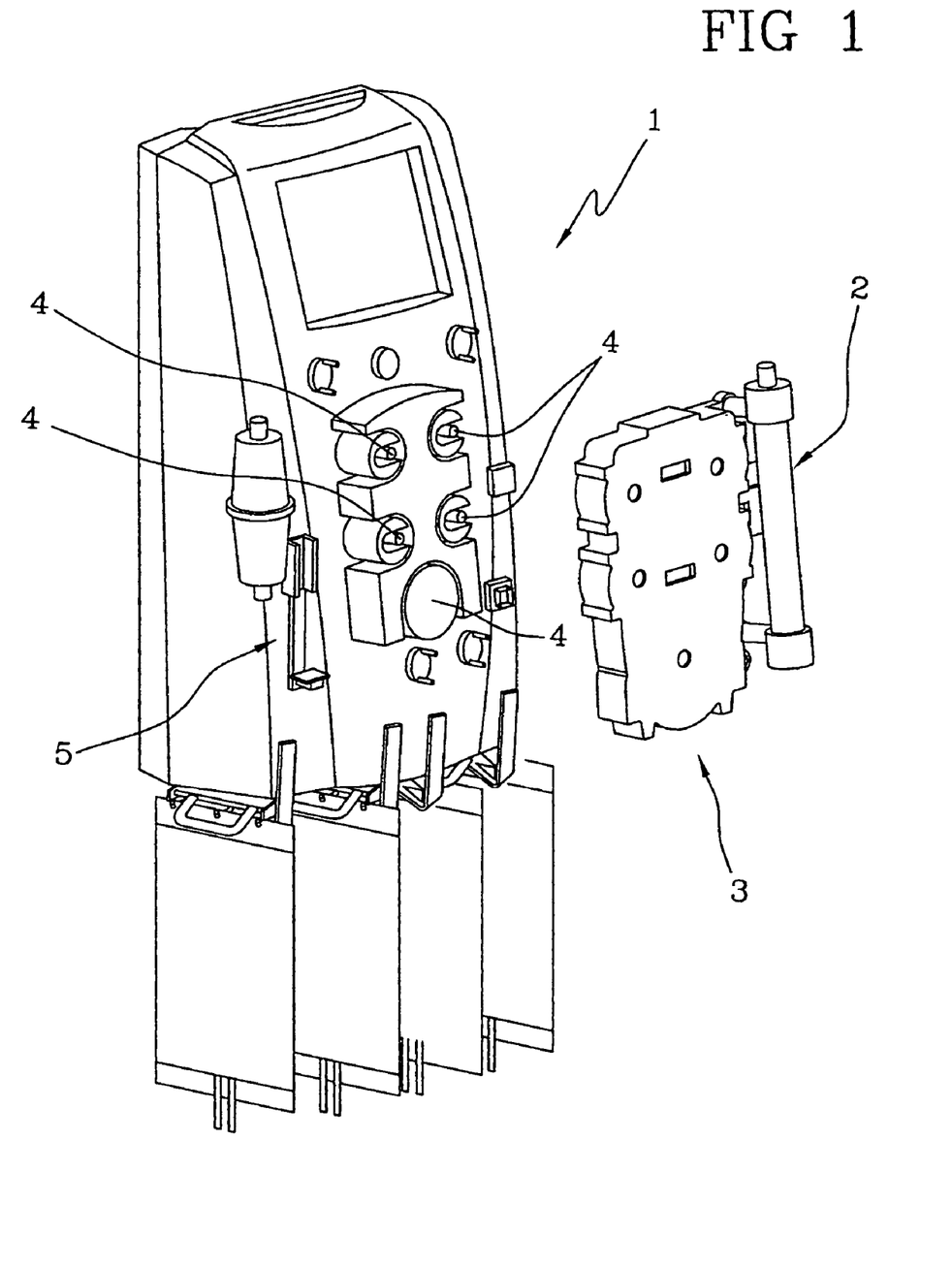
FIG. 1 shows a machine for extracorporeal blood treatment, provided with an infusion device according to the invention.
Figure 2:
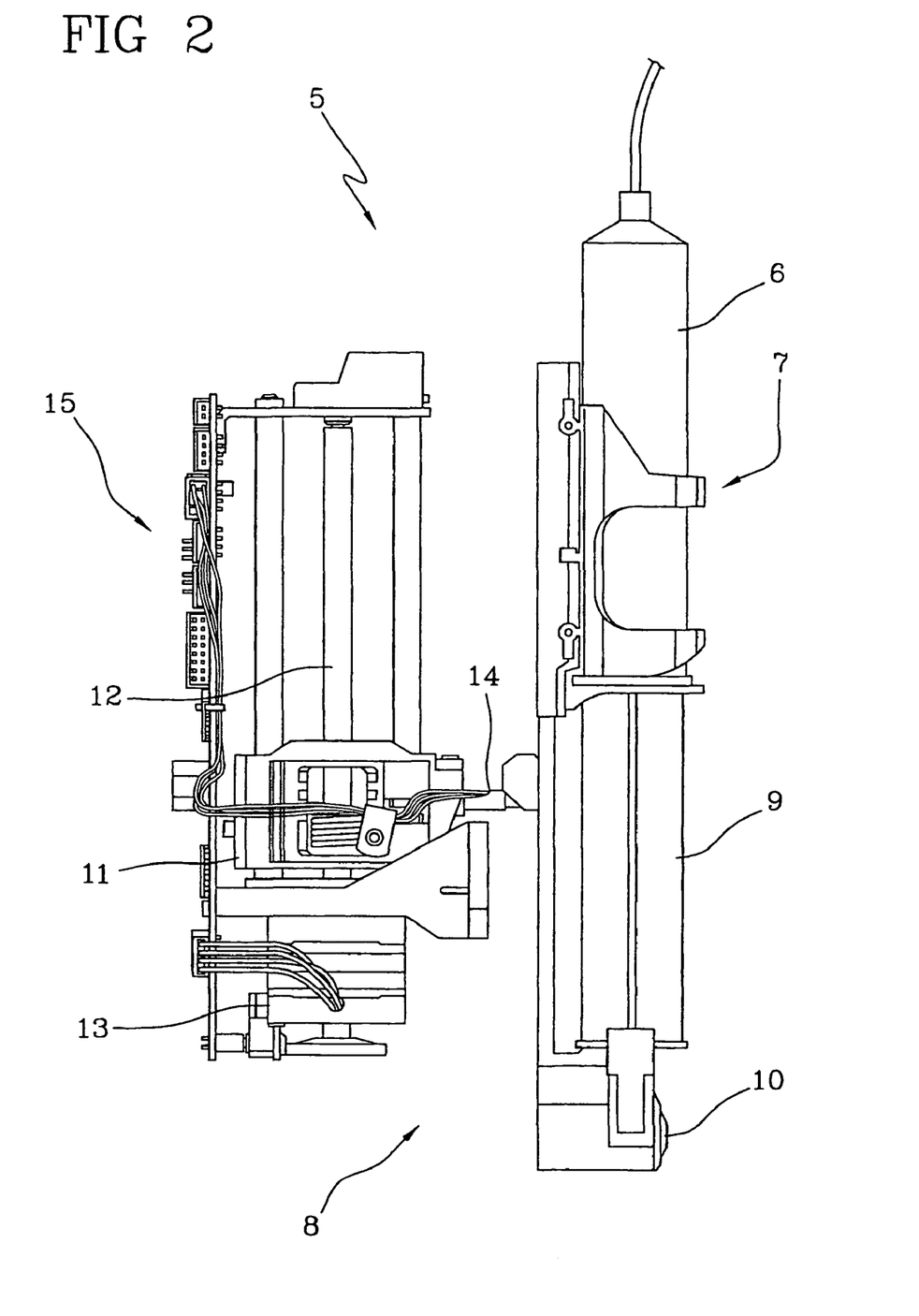
FIG. 2 is an enlarged scale view of the infusion device of FIG. 1.

Legends of FIGS. 1 and 2:
1 A machine for extracorporeal blood treatment
2 A device for blood treatment
3 Fluid distribution circuit
4 Tube deformation pumps (peristaltic)
5 Infusion device
6 Syringe
7 Syringe holder
8 Actuator of the infusion device
9 Syringe plunger
10 Actuator pusher
11 Actuator truck
12 Endless screw translator
13 Actuator motor
14 Force sensor
15 Actuator controller

1 denotes in its entirety a machine for extracorporeal blood treatment which, in the embodiment, is a dialysis machine for treatment of kidney failure, for treating: hemodialysis, pure ultrafiltration, hemofiltration, hemodiafiltration, therapeutic plasma exchange. The machine of FIG. 1 is especially suitable for intensive treatment of acute renal insufficiency.

A blood treatment device 2 (dialyzer filter) is associated to the dialysis machine 1, as is a fluid distribution circuit 3 which is connected to the blood treatment device 2.

In FIG. 1, for the sake of simplicity and clarity in the drawing, only the support to which the fluid distribution circuit is associated is illustrated.

In particular, the fluid distribution circuit comprises an extracorporeal blood circuit, provided with an arterial line and a venous line, as well as a circuit for the circulation of various treatment fluids which can comprise, in accordance with the selected treatment, a line supplying the fresh dialysis fluid to the treatment device 2, a discharge line of a waste fluid exiting from the treatment device 2, one or more infusion lines of various medical liquids (substitution liquid, anticoagulant, etc). In the illustrated embodiment the blood treatment device 2 and the fluid distribution circuit 3 are of the single-use type, or in any case of the disposable type.

The machine 1 is also provided with means for circulating various fluids along the lines, which comprise various tube deformation pumps 4 of the peristaltic type.

The means for circulation of the anticoagulant comprise an infusion device 5 which is particularly suitable for administering low-flow rates of liquid. The infusion device 5 comprises, in the embodiment, a syringe pump.

The machine 1 frontally exhibits a housing for receiving a syringe 6 containing the anticoagulant liquid to be infused. The machine 1 is also provided with means, of known type, for fixing the syringe in the housing, denoted by 7.

The syringe 6 is connected to an infusion line of anticoagulant, which terminates in the arterial line.

The infusion liquid 5 comprises an actuator 8 for commanding a movement of the plunger 9 of the syringe. The actuator 8 is a linear actuator and comprises a part which is mobile along a straight movement direction. This mobile part comprises a pusher 10 destined to interact contactingly with the plunger 9 in order to exert a pushing force aimed at causing an infusion flow rate.

The actuator 8 also comprises, in this embodiment, a truck 11 supporting the pusher 10 which is guided by an endless screw translator 12 commanded in rotation by an electric step motor 13.

The infusion device 5 comprises a force sensor 14 for measuring a force applied on the pusher 10. The force sensor 14 comprises, in the illustrated embodiment, an analog force transducer (for example a load cell) which continuously measures the push force applied on the pusher 10.

In the illustrated embodiment the force sensor 14 is arranged between the linearly mobile truck 11 and the pusher 10. It is however possible to arrange this differently, for example in a zone of the syringe housing for operating on the front part of the syringe, or in other positions besides.

During use the force sensor 14 enables a measuring of the infusion force applied on the plunger 9 of the syringe 6.

The infusion device 5 is also provided with a controller 15 which commands the actuator 8, and which receives the signals sent by the force sensor 14.

Figure 3:
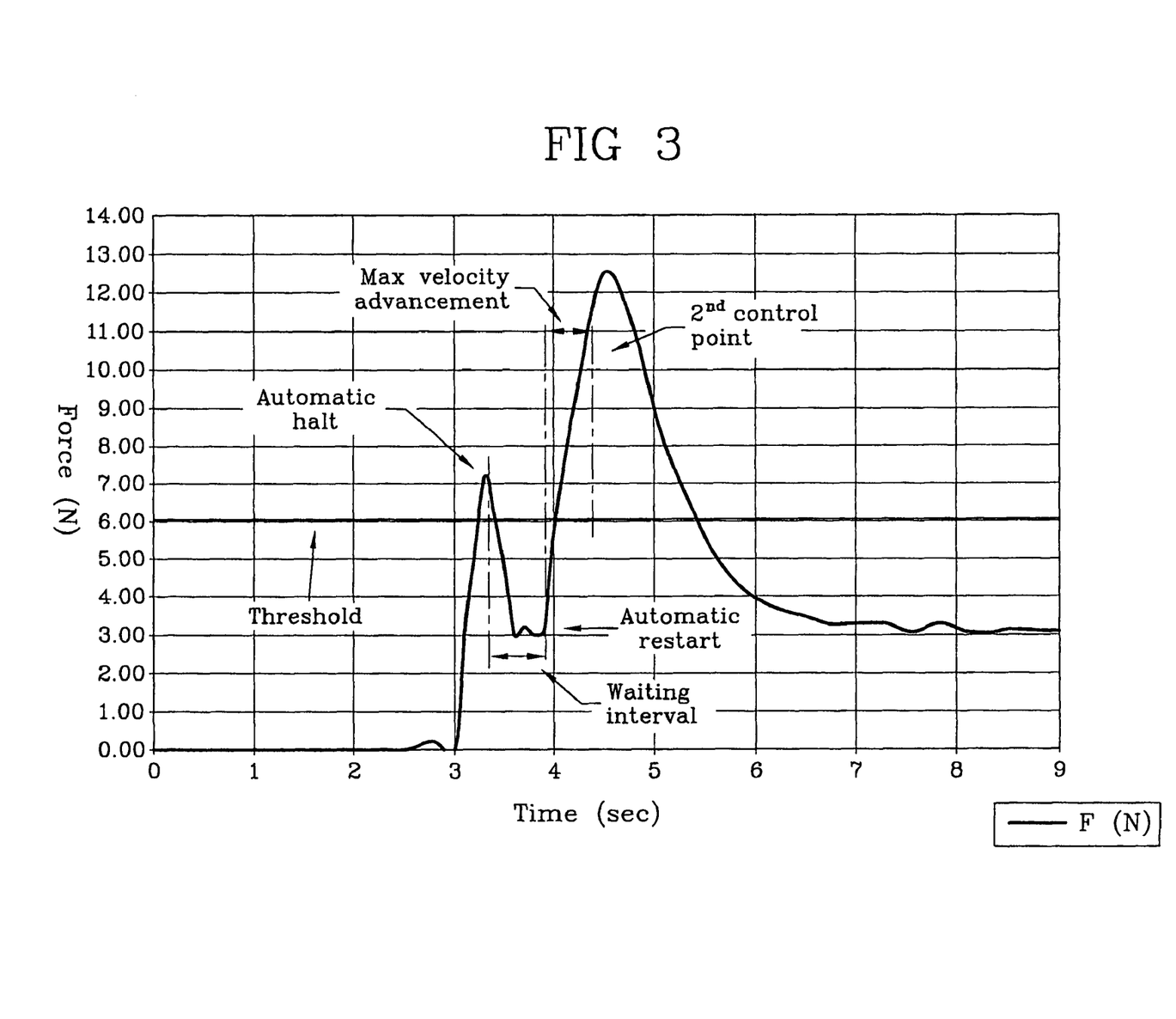
FIG. 3 is a diagram of the force applied on the pusher of the infusion device, according to a time scale, during the syringe-loading control procedure of the infusion device of FIG. 2.

The controller is programmed to perform, before administering the anticoagulant to the blood in the extracorporeal circuit, the following operations of a control procedure for correct syringe loading in relation to the pusher:

- calculating at least a first value of a parameter of an infusion force; this indicative parameter is the push force on the plunger 9 measured, in the example, by the force sensor 14 predisposed between the truck 11 and the pusher 10 for detecting the push force applicable on the plunger 9 of the syringe 6; the reading of the push force applied on the syringe can be done while the operator manually activates the advancement of the pusher 10 using a command button of the actuator 8 provided on the machine 1; alternatively the reading can be done while the controller 15 commands, automatically, a gradual advancement of the pusher 10 in the direction which causes the infusion liquid to be dispensed; in substance, the control procedure includes a phase of gradual displacement of the pusher 10 towards a contact position with the plunger—a displacement performed either manually by an operator or automatically by a programmed controller—during the course of which the infusion force applied on the syringe 6 (or other parameter correlated to the force) is monitored;
- verifying whether the previously-determined first value F1 satisfies a first predetermined relation with a first reference value; this relation is, in the present embodiment, $F1 \geq F_{threshold}$, where $F_{threshold}$ is the predetermined reference value;
- providing a first command signal to the actuator 8 in consequence of the verification performed previously; in this case, if $F1 \geq F_{threshold}$, the controller is programmed to block the actuator 8 so as to stop, or at least slow down, the advancement of the pusher 10; if, on the other hand, $F1 < F_{threshold}$, the run of the pusher 10 is not influenced, but continues according to the set modalities, while the measuring of the value of the push force is continuously compared with the maximum threshold value $F_{threshold}$, until the threshold is exceeded, causing, as above-mentioned, the blocking or the slowing down of the actuator 8;
- providing a second command signal to the actuator; once the first command signal (i.e. the blocking signal of the actuator 8) has been emitted, the controller is programmed to issue a second command signal after a predetermined time interval (for example half a second); the second signal commands the re-activation of the actuator 8 in order to restart or accelerate the advancement run of the pusher 10; this reactivation is guided by a programmed controller; in this case the reactivation includes advancing the pusher 10 at a speed which is close to maximum velocity (or in any case at least 80% of maximum velocity), at most for a predetermined time Tc (for example Tc might be equal to a few tenths of a second) by the program used by the controller; once the above time has lapsed, the controller, if it has not yet intervened to halt the advancement of the pusher, is programmed to halt the advancement in any case;
- calculating, at the end of the advancement run or immediately after it, at least a second value of a parameter which is indicative of an infusion force; in the embodiment this parameter is, as before, the push force of the pusher 10 measured by the force sensor 14; the second value of this force measured in this reactivation phase is indicated by G1;
- verifying whether the second value G1, first measured, satisfies a second prefixed relation with a second reference value; in the preferred embodiment, the second relation is equal to the first, that is $G1 \geq G_{threshold}$, where $G_{threshold}$ is a maximum threshold value which, in this particular case, is equal to the threshold $F_{threshold}$;
- emitting a control signal in consequence of the verification; in the embodiment, if $G1 \geq G_{threshold}$, the controller emits a signal notifying the user of the loading-complete and providing a consent signal for initiating the infusion process, inasmuch as the procedure has verified that the actuator 8 has correctly engaged with the syringe 6; at the same time the controller issues a command signal to halt advancement of the pusher 10 into a position which is correct for starting the infusion; if, on the other hand, $G1 < G_{threshold}$, the controller does not interrupt the advancement course of the pusher and once more monitors the push force, with the aim of detecting any exceeding of the first threshold $F_{threshold}$.

The control procedure includes automatically halting or slowing down the advancement course of the pusher on exceeding a threshold of the pushing force, and then automatically restarting the advancement run after a brief pause to verify if the above-cited threshold—or other value close thereto—is newly exceeded. The second over-value ensures that the first one, rather than being effective pushing contact between the pusher 10 and the plunger 9, is not due to an accidental occurrence, such as an accidental jolt of the syringe, a noise disturbance on the electrical signal of the force sensor 14, or other chance and unpredictable phenomena.

Figure 4:
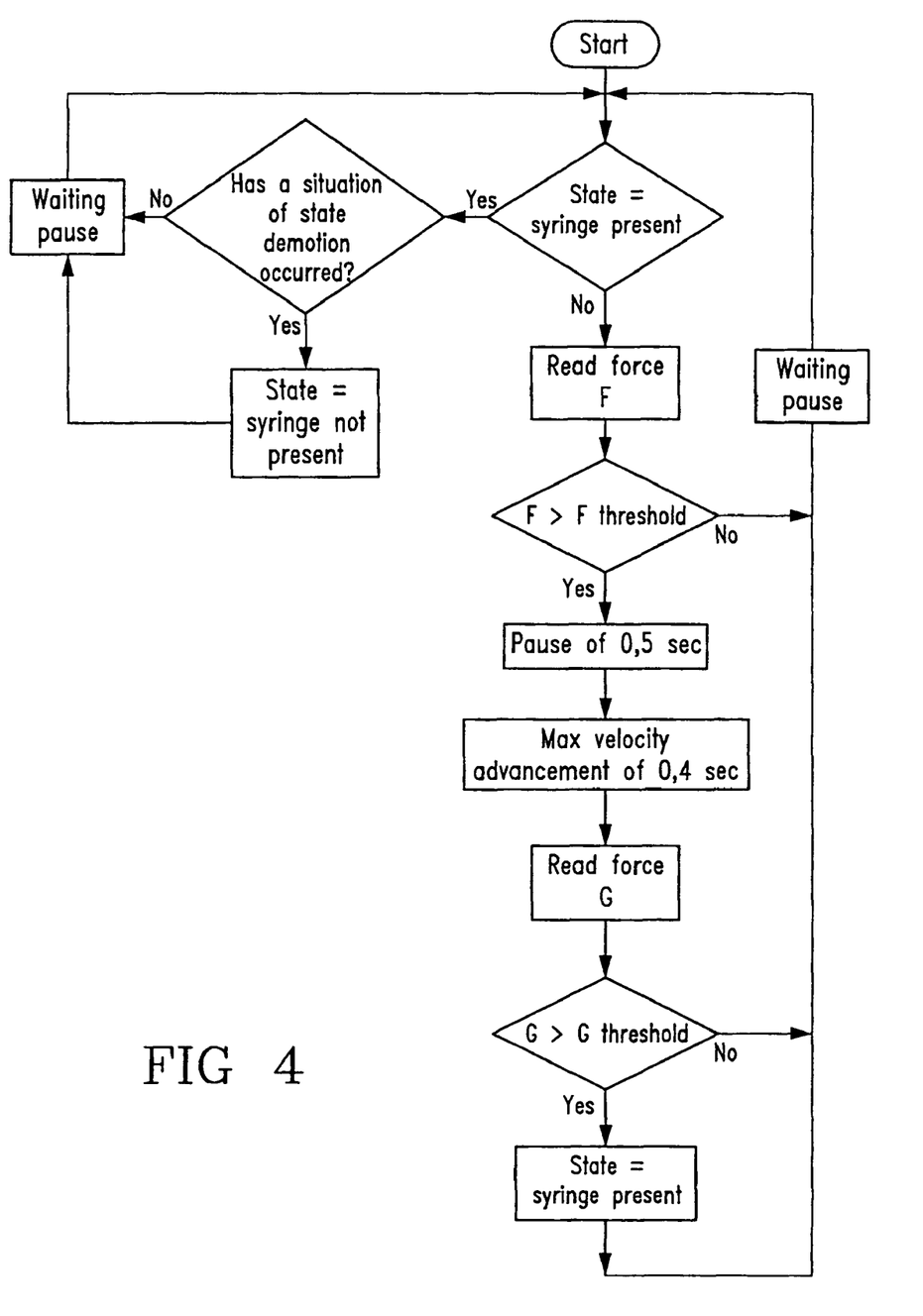
FIG. 4 is a block diagram describing the control algorithm for correct syringe loading.

The control algorithm use by the controller 15 to carry out the control on the correct readying of the infusion device 5, as above-described, is set out schematically in the block diagram of FIG. 4.

The software program, which comprises the instructions for enabling the controller 15 to carry out the above-described operations, can be memorised on a magnetic and/or optical support, can be stored on the computer memory, can be recorded onto an electrical or electromagnetic support, and can be memorised on a "read-only" memory.

The invention claimed is:

1. A process for controlling an infusion device, wherein the infusion device comprises a variable-volume container of the infusion liquid and an actuator for exerting an infusion force able to cause infusion of the liquid, the process comprising stages of:
   - activating the actuator;
   - determining at least a first value of a parameter indicating an infusion force;
   - verifying whether the first value satisfies a first predetermined relation with a first reference value;
   - emitting at least one command signal for generating a variation in the functioning of the actuator if the relation is satisfied, the at least one command signal comprising a first command signal to the actuator and a second command signal to the actuator, a predetermined time interval lapses between the stage of emitting a first signal and the stage of emitting a second signal;
   - determining at least a second value of a parameter indicating an infusion force;
   - verifying whether the second value satisfies a second predetermined relation with a second reference value; and emitting a further signal in consequence of the verification of the at least a second value, wherein the infusion liquid is a blood anticoagulant.

2. The process of claim 1, wherein the first command signal is a signal which blocks or slows down the actuator.

3. The process of claim 2, wherein the signal which blocks or slows down the actuator is emitted if the first relation is satisfied.

4. The process of claim 1, wherein the second command signal is a signal which activates or accelerates the actuator.

5. The process of claim 1, wherein the second command signal comprises an activation of the actuator for a predetermined duration.

6. The process of claim 1, wherein the second command signal comprises an activation of the actuator with an infusion force which is close to a maximum force available for the actuator.

7. The process of claim 1, wherein the further signal is a signal of consent or an alarm according to whether the second relation is satisfied or not.

8. The process of claim 1, wherein the parameter relating to the first value is also the parameter relating to the second value.

9. The process of claim 1, wherein the first predetermined relation is equal to the second predetermined relation.

10. The process of claim 1, wherein the first reference value is equal to the second reference value.

11. The process of claim 1, wherein the stages are automatically commanded by a controller.

12. The process of claim 1, wherein the stage of activation is performed on manual command by an operator, while other stages thereof are commanded automatically by a controller.

13. The process of claim 1, wherein the infusion device is operatively associated to an extracorporeal blood circuit.

14. The process of claim 1 used for checking the correct reciprocal positioning of said variable-volume container and said actuator.

15. A process for controlling an infusion device, wherein the infusion device comprises a variable-volume container of the infusion liquid and an actuator for exerting an infusion force able to cause infusion of the liquid, the process comprising stages of:

activating the actuator;

determining at least a first value of a parameter indicating an infusion force;

verifying whether the first value satisfies a first predetermined relation with a first reference value;

emitting at least one command signal for generating a variation in the functioning of the actuator if the relation is satisfied, the at least one command signal comprising a first command signal to the actuator and a second command signal to the actuator, a predetermined time interval lapses between the stage of emitting a first signal and the stage of emitting a second signal;

determining at least a second value of a parameter indicating an infusion force;

verifying whether the second value satisfies a second predetermined relation with a second reference value; and emitting a further signal in consequence of the verification of the at least a second value, wherein the infusion device is operatively associated to an extracorporeal blood circuit.

16. The process of claim 15, wherein the first command signal is a signal which blocks or slows down the actuator.

17. The process of claim 16, wherein the signal which blocks or slows down the actuator is emitted if the first relation is satisfied.

18. The process of claim 15, wherein the second command signal is a signal which activates or accelerates the actuator.

19. The process of claim 15, wherein the second command signal comprises an activation of the actuator for a predetermined duration.

20. The process of claim 15, wherein the second command signal comprises an activation of the actuator with an infusion force which is close to a maximum force available for the actuator.

21. The process of claim 15, wherein the further signal is a signal of consent or an alarm according to whether the second relation is satisfied or not.

22. The process of claim 15, wherein the parameter relating to the first value is also the parameter relating to the second value.

23. The process of claim 15, wherein the first predetermined relation is equal to the second predetermined relation.

24. The process of claim 15, wherein the first reference value is equal to the second reference value.

25. The process of claim 15, wherein the stages are automatically commanded by a controller.

26. The process of claim 15, wherein the stage of activation is performed on manual command by an operator, while other stages thereof are commanded automatically by a controller.

27. The process of claim 15 used for checking the correct reciprocal positioning of said variable-volume container and said actuator.

28. A process for controlling an infusion device, wherein the infusion device comprises a variable-volume container of the infusion liquid and an actuator for exerting an infusion force able to cause infusion of the liquid, the process comprising stages of:

activating the actuator;

determining at least a first value of a parameter indicating an infusion force;

verifying whether the first value satisfies a first predetermined relation with a first reference value;

emitting at least one command signal for generating a variation in the functioning of the actuator if the relation is satisfied, the at least one command signal comprising a first command signal to the actuator and a second command signal to the actuator, a predetermined time interval lapses between the stage of emitting a first signal and the stage of emitting a second signal;

determining at least a second value of a parameter indicating an infusion force;

verifying whether the second value satisfies a second predetermined relation with a second reference value; and emitting a further signal in consequence of the verification of the at least a second value, wherein the second command signal comprises an activation of the actuator with an infusion force which is close to a maximum force available for the actuator.

29. A tangible, machine-readable medium having instructions for at least one controller recorded thereon, the medium comprising:

instructions for activating an actuator;

instructions for determining at least a first value of a parameter indicating an infusion force;

instructions for verifying whether the first value satisfies a first predetermined relation with a first reference value;

instructions for emitting at least one command signal for generating a variation in the functioning of the actuator if the relation is satisfied, the at least one command signal comprising a first command signal to the actuator and a second command signal to the actuator, a predetermined time interval lapses between the stage of emitting a first signal and the stage of emitting a second signal, the second command signal comprising an activation of the actuator with an infusion force which is close to a maximum force available for the actuator;

instructions for determining at least a second value of a parameter indicating an infusion force;

instructions for verifying whether the second value satisfies a second predetermined relation with a second reference value; and instructions for emitting a further signal in consequence of the verification of the at least a second value.

30. The medium of claim 29, wherein the medium comprises at least one of a means for magnetic and/or optical recording, a computer memory, an electrical or electromagnetic support, and a read-only memory.

* * * * *

UNITED STATES PATENT AND TRADEMARK OFFICE
CERTIFICATE OF CORRECTION

PATENT NO. : 7,758,547 B2　　　　　　　　　　　　　　　　　　　　　　　　　　　　Page 1 of 1
APPLICATION NO. : 11/104446
DATED : July 20, 2010
INVENTOR(S) : Tonelli et al.

It is certified that error appears in the above-identified patent and that said Letters Patent is hereby corrected as shown below:

On the Title page, item (30) under "Foreign Application Priority Data", delete "(TW)" and insert --(IT)--.

Signed and Sealed this

Twelfth Day of October, 2010

David J. Kappos
*Director of the United States Patent and Trademark Office*